(12) United States Patent
Jackson

(10) Patent No.: US 8,377,102 B2
(45) Date of Patent: Feb. 19, 2013

(54) POLYAXIAL BONE ANCHOR WITH SPLINE CAPTURE CONNECTION AND LOWER PRESSURE INSERT

(76) Inventor: Roger P. Jackson, Prairie Village, KS (US)

( * ) Notice: Subject to any disclaimer, the term of this patent is extended or adjusted under 35 U.S.C. 154(b) by 216 days.

(21) Appl. No.: 12/661,986

(22) Filed: Mar. 26, 2010

(65) Prior Publication Data

US 2010/0191293 A1 Jul. 29, 2010

Related U.S. Application Data

(63) Continuation-in-part of application No. 12/587,244, filed on Oct. 2, 2009, which is a continuation of application No. 10/818,554, filed on Apr. 5, 2004, now Pat. No. 7,662,175, which is a continuation-in-part of application No. 10/651,003, filed on Aug. 28, (Continued)

(51) Int. Cl.
*A61B 17/70* (2006.01)
(52) U.S. Cl. .......................... 606/269; 606/266; 606/304
(58) Field of Classification Search .................. 606/246, 606/247, 266, 267, 270, 302, 304, 305, 308, 606/309
See application file for complete search history.

(56) References Cited

U.S. PATENT DOCUMENTS

| | | | |
|---|---|---|---|
| 2,346,346 A | 4/1944 | Anderson | |
| 2,362,999 A | 11/1944 | Elmer | |
| 2,531,892 A | 11/1950 | Reese | |
| 2,813,450 A | 11/1957 | Dzus | |
| 3,013,244 A | 12/1961 | Rudy | |
| 4,033,139 A | 7/1977 | Frederick | |
| 4,759,672 A | 7/1988 | Nilsen et al. | |
| 4,790,297 A | 12/1988 | Luque | |
| 4,946,458 A | 8/1990 | Harms et al. | |
| 5,019,080 A | 5/1991 | Hemer | |
| 5,129,388 A | 7/1992 | Vignaud et al. | |
| 5,207,678 A | 5/1993 | Harms et al. | |
| 5,261,912 A | 11/1993 | Frigg | |
| 5,312,404 A | 5/1994 | Asher et al. | |
| 5,360,431 A | 11/1994 | Puno et al. | |
| 5,395,371 A | 3/1995 | Miller et al. | |
| 5,429,639 A | 7/1995 | Judet | |

(Continued)

FOREIGN PATENT DOCUMENTS

DE 19507141 9/1996
EP 1121902 8/2001

(Continued)

OTHER PUBLICATIONS

*EBI Omega 21* Brochure, EBI Spine Systems, pub. 1999.

(Continued)

*Primary Examiner* — Thomas J Sweet
*Assistant Examiner* — Christopher D Prone
(74) *Attorney, Agent, or Firm* — John C. McMahon

(57) ABSTRACT

A medical implant assembly includes a polyaxial bone anchor having a shank with an upper portion, a receiver, a retainer for holding the shank upper portion in the receiver, a lower compression insert with surfaces for closely receiving an elongate connecting member and a closure structure that may independently engage the lower compression insert to lock the shank with respect to the receiver while selectively not locking the elongate member. Projections or splines of the shank upper portion mate with holding pockets on the retainer. The bone anchor includes a shank upper surface exclusively engaging the lower compression insert that is spaced from the retainer, the retainer and shank being configured for polyaxial motion with respect to the receiver prior to locking.

16 Claims, 6 Drawing Sheets

Related U.S. Application Data 2003, now Pat. No. 8,137,386, and a continuation of application No. 10/464,633, filed on Jun. 18, 2003, now Pat. No. 6,716,214, application No. 12/661,986, which is a continuation-in-part of application No. 12/154,460, filed on May 23, 2008, now Pat. No. 8,257,396, which is a continuation-in-part of application No. 11/140,343, filed on May 27, 2005, now Pat. No. 7,776,067, and a continuation-in-part of application No. 10/818,555, filed on Apr. 5, 2004, now Pat. No. 8,052,724, which is a continuation of application No. 10/464,633, and a continuation-in-part of application No. 10/651,003, application No. 12/661,986, which is a continuation-in-part of application No. 12/290,244, filed on Oct. 29, 2008, now Pat. No. 7,967,850, which is a continuation-in-part of application No. 11/522,503, filed on Sep. 14, 2006, now Pat. No. 7,766,915, which is a continuation-in-part of application No. 11/024,543, filed on Dec. 20, 2004, now Pat. No. 7,204,838.

(60) Provisional application No. 61/211,169, filed on Mar. 27, 2009, provisional application No. 60/931,362, filed on May 23, 2007, provisional application No. 61/000,964, filed on Oct. 30, 2007.

(56) References Cited

U.S. PATENT DOCUMENTS

| | | |
|---|---|---|
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,496,321 A | 3/1996 | Puno et al. |
| 5,554,157 A | 9/1996 | Errico et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,426 A | 3/1997 | Ralph et al. |
| 5,647,873 A | 7/1997 | Errico et al. |
| 5,669,911 A | 9/1997 | Errico et al. |
| 5,672,176 A | 9/1997 | Biedermann et al. |
| 5,681,319 A | 10/1997 | Biedermann et al. |
| 5,690,630 A | 11/1997 | Errico et al. |
| 5,716,356 A | 2/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,938,663 A | 8/1999 | Petreto |
| 5,954,725 A | 9/1999 | Sherman et al. |
| 5,961,517 A | 10/1999 | Biedermann et al. |
| 5,964,760 A | 10/1999 | Richelsoph |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,214,012 B1 | 4/2001 | Karpman et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Jusis et al. |
| 6,533,786 B1 | 3/2003 | Needham et al. |
| 6,547,790 B2 | 4/2003 | Harkey, III et al. |
| 6,551,320 B2 | 4/2003 | Liebermann |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,526 B1 | 11/2003 | Arafiles |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |

| | | | |
|---|---|---|---|
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,677 B1 | 5/2005 | Lin |
| 6,932,817 B2 | 8/2005 | Baynham et al. |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,426 B2 | 10/2006 | Moumene et al. |
| 7,128,743 B2 | 10/2006 | Metz-Stavenhagen |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,445,627 B2 | 11/2008 | Hawkes et al. |
| 7,476,228 B2 | 1/2009 | Abdou |
| 7,479,156 B2 | 1/2009 | Lourdel et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,640 B2 | 5/2009 | Ziolo et al. |
| 7,530,992 B2 | 5/2009 | Biedermann et al. |
| 7,559,943 B2 | 7/2009 | Mjuwid |
| 7,563,264 B2 | 7/2009 | Landry et al. |
| 7,563,275 B2 | 7/2009 | Falahee et al. |
| 7,569,061 B2 | 8/2009 | Colleran |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,604,656 B2 | 10/2009 | Shluzas |
| 7,611,518 B2 | 11/2009 | Walder et al. |
| 7,615,068 B2 | 11/2009 | Timm et al. |
| 7,621,941 B2 | 11/2009 | Schlapfer et al. |
| 7,625,394 B2 | 12/2009 | Molz, IV et al. |
| 7,641,674 B2 | 1/2010 | Young |
| 7,645,294 B2 | 1/2010 | Kalfas et al. |
| 7,648,522 B2 | 1/2010 | David |
| 8,002,806 B2 * | 8/2011 | Justis .......................... 606/264 |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0172031 A1 * | 9/2004 | Rubecamp et al. ............ 606/73 |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0055026 A1 | 3/2005 | Biedermann et al. |
| 2005/0070899 A1 | 3/2005 | Doubler et al. |
| 2005/0080415 A1 | 4/2005 | Keyer et al. |

| | | |
|---|---|---|
| 2005/0096654 A1 | 5/2005 | Lin |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203516 A1 | 9/2005 | Biedermann et al. |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0260058 A1 | 11/2005 | Casagne, III |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Liebermann |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079899 A1 | 4/2006 | Ritland |
| 2006/0084981 A1 | 4/2006 | Shluzas |
| 2006/0084989 A1 | 4/2006 | Dickinson et al. |
| 2006/0084993 A1 | 4/2006 | Landry et al. |
| 2006/0084995 A1 | 4/2006 | Biedermann et al. |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106383 A1 | 5/2006 | Biedermann et al. |
| 2006/0116677 A1 | 6/2006 | Burd et al. |
| 2006/0129147 A1 | 6/2006 | Biedermann et al. |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfiled et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0195098 A1 | 8/2006 | Schumacher |
| 2006/0200128 A1 | 9/2006 | Mueller |
| 2006/0200131 A1 | 9/2006 | Chao et al. |
| 2006/0200149 A1 | 9/2006 | Hoy et al. |
| 2006/0212034 A1 | 9/2006 | Triplett et al. |
| 2006/0217716 A1 | 9/2006 | Baker et al. |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0247624 A1 | 11/2006 | Banouskou et al. |
| 2006/0247631 A1 | 11/2006 | Ahn et al. |
| 2006/0247636 A1 | 11/2006 | Yuan et al. |
| 2006/0247779 A1 | 11/2006 | Gordon et al. |
| 2006/0264933 A1 | 11/2006 | Baker et al. |
| 2006/0264936 A1 | 11/2006 | Partin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0293659 A1 | 12/2006 | Alvarez |
| 2006/0293665 A1 | 12/2006 | Shluzas |
| 2006/0293666 A1 | 12/2006 | Matthis et al. |
| 2007/0016188 A1 | 1/2007 | Boehm, Jr. et al. |
| 2007/0016198 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049933 A1 | 3/2007 | Ahn et al. |
| 2007/0055235 A1 | 3/2007 | Janowski et al. |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073291 A1 | 3/2007 | Cordaro et al. |
| 2007/0078460 A1 | 4/2007 | Frigg et al. |
| 2007/0083199 A1 | 4/2007 | Baccelli |
| 2007/0088357 A1 | 4/2007 | Johnson et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123867 A1 | 5/2007 | Kirschman |
| 2007/0123870 A1 | 5/2007 | Jeon et al. |
| 2007/0161986 A1 | 7/2007 | Levy |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173819 A1 | 7/2007 | Sandlin |
| 2007/0173820 A1 | 7/2007 | Trieu |
| 2007/0173828 A1 | 7/2007 | Firkins et al. |
| 2007/0191839 A1 | 8/2007 | Justis et al. |
| 2007/0198014 A1 | 8/2007 | Graf et al. |

| | | | | | | |
|---|---|---|---|---|---|---|
| 2007/0208344 A1 | 9/2007 | Young | | 2008/0312655 A1 | 12/2008 | Kirschman et al. |
| 2007/0225707 A1 | 9/2007 | Wisnewski et al. | | 2008/0312692 A1 | 12/2008 | Brennan et al. |
| 2007/0225711 A1 | 9/2007 | Ensign | | 2008/0312696 A1 | 12/2008 | Battlers et al. |
| 2007/0233078 A1 | 10/2007 | Justis et al. | | 2008/0312701 A1 | 12/2008 | Batters et al. |
| 2007/0233080 A1 | 10/2007 | Na et al. | | 2009/0005787 A1 | 1/2009 | Crall et al. |
| 2007/0233086 A1 | 10/2007 | Harms et al. | | 2009/0005813 A1 | 1/2009 | Crall et al. |
| 2007/0233087 A1 | 10/2007 | Schlapfer | | 2009/0005814 A1 | 1/2009 | Miller et al. |
| 2007/0250061 A1 | 10/2007 | Chin et al. | | 2009/0012567 A1 | 1/2009 | Biedermann et al. |
| 2007/0260246 A1 | 11/2007 | Biedermann | | 2009/0018591 A1 | 1/2009 | Hawkes et al. |
| 2007/0270806 A1 | 11/2007 | Foley et al. | | 2009/0024169 A1 | 1/2009 | Triplett et al. |
| 2007/0270807 A1 | 11/2007 | Armstrong et al. | | 2009/0030457 A1 | 1/2009 | Janowski et al. |
| 2007/0270810 A1 | 11/2007 | Sanders | | 2009/0036929 A1 | 2/2009 | Reglos et al. |
| 2007/0270813 A1 | 11/2007 | Garamszegi | | 2009/0036932 A1 | 2/2009 | Rouyer et al. |
| 2007/0270815 A1 | 11/2007 | Johnson et al. | | 2009/0036934 A1 | 2/2009 | Biedermann et al. |
| 2007/0270830 A1 | 11/2007 | Morrison | | 2009/0062860 A1 | 3/2009 | Frasier et al. |
| 2007/0270831 A1 | 11/2007 | Dewey et al. | | 2009/0062865 A1 | 3/2009 | Schumacher |
| 2007/0270832 A1 | 11/2007 | Moore | | 2009/0062867 A1 | 3/2009 | Schumacher |
| 2007/0270835 A1 | 11/2007 | Wisnewski | | 2009/0062914 A1 | 3/2009 | Marino |
| 2007/0270839 A1 | 11/2007 | Jeon et al. | | 2009/0069849 A1 | 3/2009 | Oh et al. |
| 2007/0288004 A1 | 12/2007 | Alvarez | | 2009/0069852 A1 | 3/2009 | Farris et al. |
| 2008/0009862 A1 | 1/2008 | Hoffman | | 2009/0069853 A1 | 3/2009 | Schumacher |
| 2008/0009864 A1 | 1/2008 | Forton et al. | | 2009/0076550 A1 | 3/2009 | Bernhardt, Jr. et al. |
| 2008/0015578 A1 | 1/2008 | Erickson et al. | | 2009/0076552 A1 | 3/2009 | Tornier |
| 2008/0015579 A1 | 1/2008 | Whipple | | 2009/0082809 A1 | 3/2009 | Nguyen et al. |
| 2008/0015580 A1 | 1/2008 | Chao | | 2009/0082812 A1 | 3/2009 | Lewis |
| 2008/0015584 A1 | 1/2008 | Richelsoph | | 2009/0082815 A1 | 3/2009 | Zylber et al. |
| 2008/0015586 A1 | 1/2008 | Krishna et al. | | 2009/0082819 A1 | 3/2009 | Blain et al. |
| 2008/0021454 A1 | 1/2008 | Chao et al. | | 2009/0088799 A1 | 4/2009 | Yeh |
| 2008/0021455 A1 | 1/2008 | Chao et al. | | 2009/0088807 A1 | 4/2009 | Castaneda et al. |
| 2008/0021462 A1 | 1/2008 | Trieu | | 2009/0093843 A1 | 4/2009 | Lemoine et al. |
| 2008/0021464 A1 | 1/2008 | Morin et al. | | 2009/0105769 A1 | 4/2009 | Rock et al. |
| 2008/0021473 A1 | 1/2008 | Butler et al. | | 2009/0105770 A1 | 4/2009 | Berrevoets et al. |
| 2008/0027432 A1 | 1/2008 | Strauss et al. | | 2009/0105771 A1 | 4/2009 | Lei et al. |
| 2008/0039838 A1 | 2/2008 | Landry et al. | | 2009/0118772 A1 | 5/2009 | Diederich et al. |
| 2008/0039843 A1 | 2/2008 | Abdou | | 2009/0131983 A1 | 5/2009 | Biedermann |
| 2008/0045951 A1 | 2/2008 | Fanger et al. | | 2009/0138044 A1 | 5/2009 | Bergeron et al. |
| 2008/0045955 A1 | 2/2008 | Berrevoets et al. | | 2009/0138052 A1 | 5/2009 | Biedermann et al. |
| 2008/0045957 A1 | 2/2008 | Landry et al. | | 2009/0143827 A1 | 6/2009 | Levy et al. |
| 2008/0051780 A1 | 2/2008 | Vaidya et al. | | 2009/0143829 A1 | 6/2009 | Shluzas |
| 2008/0058811 A1 | 3/2008 | Alleyne et al. | | 2009/0149887 A1 | 6/2009 | Schlaepfer et al. |
| 2008/0058812 A1 | 3/2008 | Zehnder | | 2009/0163955 A1 | 6/2009 | Moumene et al. |
| 2008/0065073 A1 | 3/2008 | Perriello et al. | | 2009/0163956 A1 | 6/2009 | Biedermann et al. |
| 2008/0065075 A1 | 3/2008 | Dant | | 2009/0163961 A1 | 6/2009 | Kirschman |
| 2008/0065077 A1 | 3/2008 | Ferree | | 2009/0163963 A1 | 6/2009 | Berrevoets |
| 2008/0071273 A1 | 3/2008 | Hawkes et al. | | 2009/0182380 A1 | 7/2009 | Abdelgany |
| 2008/0071274 A1 | 3/2008 | Enisgn | | 2009/0192548 A1 | 7/2009 | Jeon et al. |
| 2008/0071277 A1 | 3/2008 | Warnick | | 2009/0192551 A1 | 7/2009 | Cianfrani et al. |
| 2008/0077139 A1 | 3/2008 | Landry et al. | | 2009/0198280 A1 | 8/2009 | Spratt et al. |
| 2008/0086131 A1 | 4/2008 | Daly et al. | | 2009/0198289 A1 | 8/2009 | Manderson |
| 2008/0086132 A1 | 4/2008 | Biedermann et al. | | 2009/0198291 A1 | 8/2009 | Kevin et al. |
| 2008/0097441 A1 | 4/2008 | Hayes et al. | | 2009/0204155 A1 | 8/2009 | Aschmann |
| 2008/0097457 A1 | 4/2008 | Warnick | | 2009/0216280 A1 | 8/2009 | Hutchinson |
| 2008/0108992 A1 | 5/2008 | Barry et al. | | 2009/0248030 A1 | 10/2009 | Butler et al. |
| 2008/0119858 A1 | 5/2008 | Potash | | 2009/0248075 A1 | 10/2009 | Ogilvie et al. |
| 2008/0140075 A1 | 6/2008 | Ensign et al. | | 2009/0248088 A1 | 10/2009 | Biedermann |
| 2008/0161859 A1 | 7/2008 | Nilsson | | 2009/0254125 A1 | 10/2009 | Predick |
| 2008/0161863 A1 | 7/2008 | Arnold et al. | | 2009/0259254 A1 | 10/2009 | Pisharodi |
| 2008/0177321 A1 | 7/2008 | Drewry et al. | | 2009/0264896 A1 | 10/2009 | Biedermann et al. |
| 2008/0177322 A1 | 7/2008 | Davis et al. | | 2009/0264933 A1 | 10/2009 | Carls et al. |
| 2008/0177332 A1 | 7/2008 | Reiley et al. | | 2009/0270916 A1 | 10/2009 | Ramsay et al. |
| 2008/0183215 A1 | 7/2008 | Altarac et al. | | 2009/0270917 A1 | 10/2009 | Boehm |
| 2008/0183223 A1 | 7/2008 | Jeon et al. | | 2009/0281571 A1 | 11/2009 | Weaver et al. |
| 2008/0195159 A1 | 8/2008 | Kloss et al. | | 2009/0281572 A1 | 11/2009 | White |
| 2008/0200956 A1 | 8/2008 | Beckwith et al. | | 2009/0281573 A1 | 11/2009 | Biedermann et al. |
| 2008/0215095 A1 | 9/2008 | Biedermann et al. | | 2009/0287253 A1 | 11/2009 | Felix et al. |
| 2008/0228229 A1 | 9/2008 | Walder et al. | | 2009/0299415 A1 | 12/2009 | Pimenta |
| 2008/0234734 A1 | 9/2008 | Walder et al. | | 2009/0306719 A1 | 12/2009 | Meyer, III et al. |
| 2008/0234756 A1 | 9/2008 | Sutcliffe et al. | | 2009/0306720 A1 | 12/2009 | Doubler et al. |
| 2008/0234759 A1 | 9/2008 | Marino | | 2009/0312804 A1 | 12/2009 | Gamache et al. |
| 2008/0249570 A1 | 10/2008 | Carson et al. | | 2009/0326582 A1 | 12/2009 | Songer et al. |
| 2008/0262548 A1 | 10/2008 | Lange et al. | | 2009/0326587 A1 | 12/2009 | Matthis et al. |
| 2008/0262556 A1 | 10/2008 | Jacofsky et al. | | 2010/0004692 A1 | 1/2010 | Biedermann et al. |
| 2008/0269742 A1 | 10/2008 | Levy et al. | | 2010/0010540 A1 | 1/2010 | Park |
| 2008/0269809 A1* | 10/2008 | Garamszegi .......... 606/305 | | 2010/0016898 A1 | 1/2010 | Shluzas |
| 2008/0287994 A1 | 11/2008 | Perez-Cruet et al. | | | | |
| 2008/0288002 A1 | 11/2008 | Crall et al. | | | | |
| 2008/0306528 A1 | 12/2008 | Winslow et al. | | EP | 1190678 | 3/2002 |
| 2008/0306533 A1 | 12/2008 | Winslow et al. | | EP | 1570795 | 9/2005 |
| 2008/0306539 A1 | 12/2008 | Cain et al. | | EP | 1579816 | 9/2005 |

FOREIGN PATENT DOCUMENTS

| | | |
|---|---|---|
| EP | 1634537 | 3/2006 |
| EP | 1925263 | 5/2008 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| FR | 2925288 | 6/2009 |
| GB | 9202745.8 | 4/1992 |
| GB | 2365345 | 2/2002 |
| WO | WO95/01132 | 1/1995 |
| WO | WO02/054966 | 7/2002 |
| WO | WO03/068088 | 8/2003 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/005198 | 1/2006 |
| WO | WO2006/012088 | 2/2006 |
| WO | WO2006/017616 | 2/2006 |
| WO | WO2006/028537 | 3/2006 |
| WO | WO2006/119241 | 11/2006 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/088731 | 7/2008 |
| WO | WO2009/015100 | 1/2009 |

OTHER PUBLICATIONS

*Claris Instrumentation* Brochure, G Med, pub. 1997.
*VLS System Variable Locking Screw* Brochure, Interpore Cross International,1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System* Brochure, Surgical Dynamics, pub. 1998-99.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.

\* cited by examiner

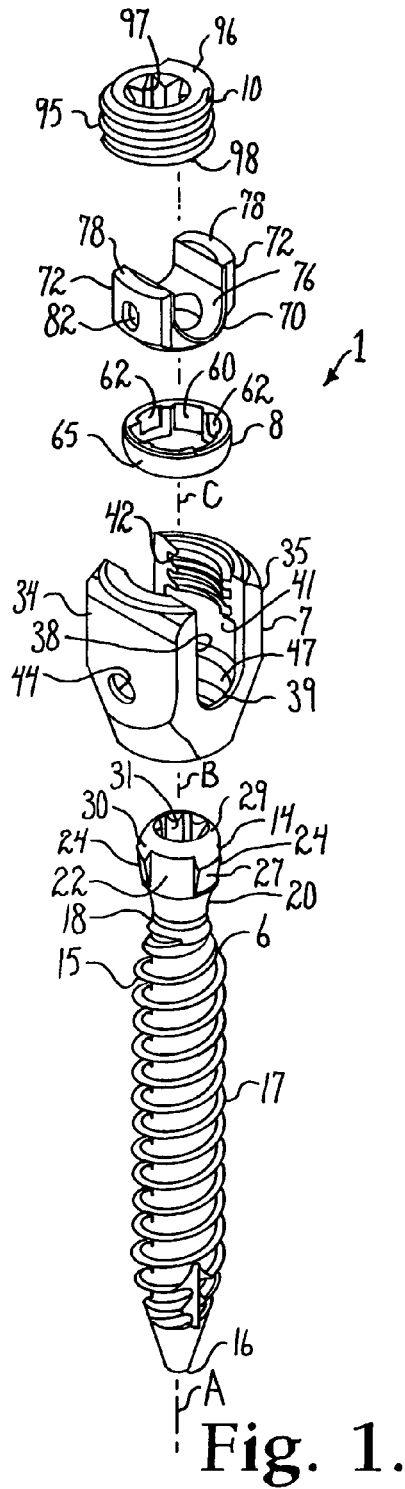
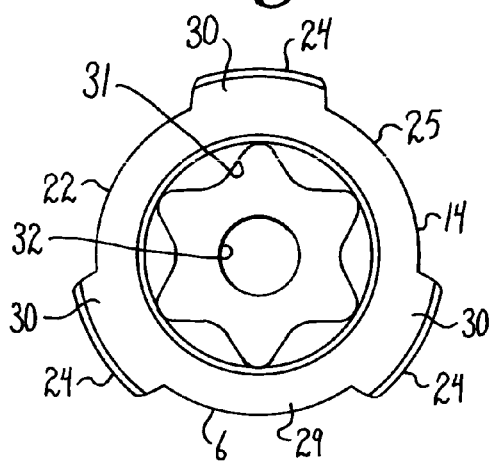
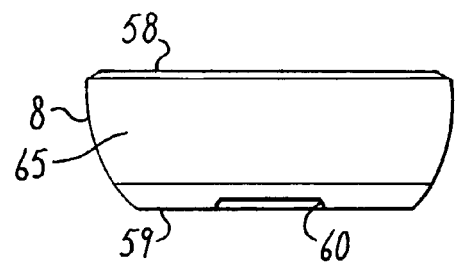
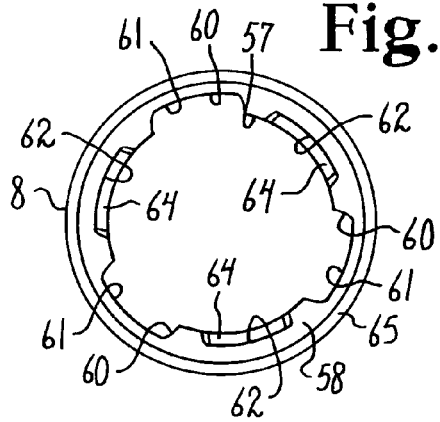

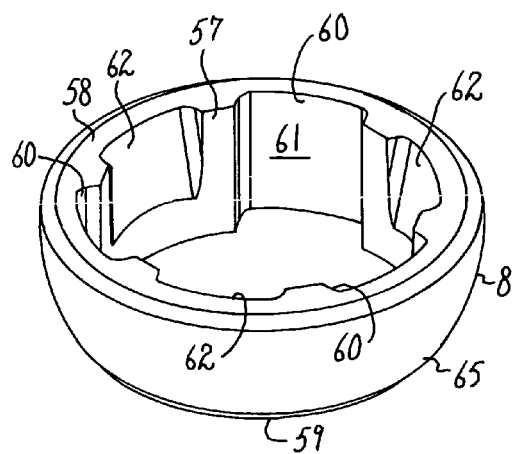
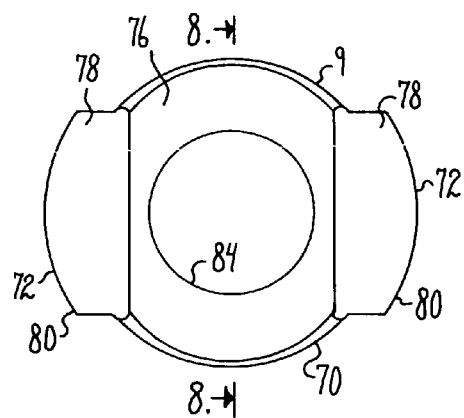
Fig. 5.   Fig. 6.
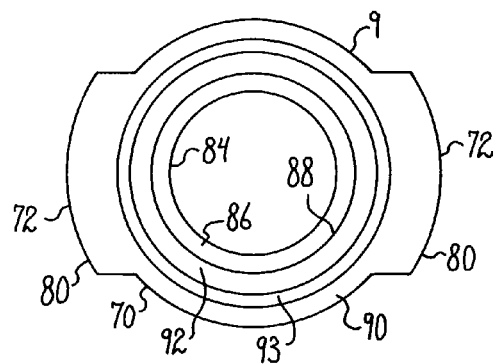
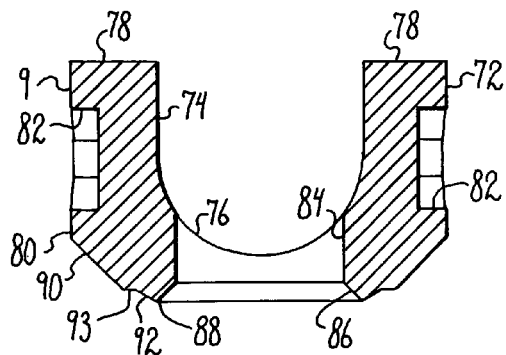
Fig. 7.   Fig. 8.

POLYAXIAL BONE ANCHOR WITH SPLINE CAPTURE CONNECTION AND LOWER PRESSURE INSERT

CROSS-REFERENCE TO RELATED APPLICATIONS

This application claims the benefit of U.S. Provisional Patent Application Ser. No. 61/211,169, filed Mar. 27, 2009 and incorporated by reference herein.

This application is also a continuation-in-part of U.S. patent application Ser. No. 12/587,244 filed Oct. 2, 2009 that is a continuation of U.S. patent application Ser. No. 10/818,554, filed Apr. 5, 2004, now U.S. Pat. No. 7,662,175, that is both a continuation-in-part of U.S. patent application Ser. No. 10/651,003 filed Aug. 28, 2003, now U.S. Pat. No. 8,137,386, and a continuation of U.S. patent application Ser. No. 10/464,633 filed Jun. 18, 2003, now U.S. Pat. No. 6,716,214, all of which are incorporated herein by reference herein.

This application is also a continuation-in-part of U.S. patent application Ser. No. 12/154,460 filed May 23, 2008 now U.S. Pat. No. 8,257,396 that claims the benefit of U.S. Provisional Application No. 60/931,362 filed May 23, 2007, and is a continuation-in-part of U.S. patent application Ser. No. 11/140,343 filed May 27, 2005, now U.S. Pat. No. 7,776,067, all of which are incorporated by reference herein. The Ser. No. 12/154,460 application is also a continuation-in-part of U.S. patent application Ser. No. 10/818,555 filed Apr. 5, 2004, now U.S. Pat. No. 8,052,724, that is a continuation of U.S. patent application Ser. No. 10/464,633 filed Jun. 18, 2003, now U.S. Pat. No. 6,716,214 and a continuation-in-part of U.S. patent application Ser. No. 10/651,003, filed Aug. 28, 2003, now U.S. Pat. No. 8,137,386, all of which are incorporated by reference herein.

This application is also a continuation-in-part of U.S. patent application Ser. No. 12/290,244 filed Oct. 29, 2008 now U.S. Pat. No. 7,967,850 that claims the benefit of U.S. Provisional application Ser. No. 61/000,964 filed Oct. 30, 2007 and that is a continuation-in-part of U.S. patent application Ser. No. 11/522,503 filed Sep. 14, 2006, now U.S. Pat. No. 7,766,915 that is a continuation-in-part of U.S. patent application Ser. No. 11/024,543 filed Dec. 20, 2004, now U.S. Pat. No. 7,204,838, all of which are incorporated by reference herein.

BACKGROUND OF THE INVENTION

The present invention is directed to polyaxial bone anchors for use in spinal surgery and especially to such anchors that are in the form of a polyaxial bone screw adapted to receive a longitudinal connecting member and secure such a member to a vertebra.

Many spinal surgery procedures require securing various implants to bone and especially to vertebrae along the spine. For example, longitudinal connecting members such as elongate rods are often required that extend along the spine to provide support to vertebrae that have been damaged or weakened due to injury, disease or the like. Such rods must be supported by certain vertebra and support other vertebra. The most common mechanism for providing such structure is to implant bone screws into certain bones which then in turn support the rod or are supported by the rod. Bone screws of this type may have a fixed head or rod receiver relative to a shank thereof. In the fixed bone screws, the receiver cannot be moved relative to the shank and the rod or other longitudinal connecting member must be favorably positioned in order for it to be placed within the receiver. This is sometimes very difficult or impossible to do so polyaxial bone screws are commonly used. Polyaxial bone screws allow rotation of the head or receiver about the shank until a desired rotational position is achieved for the receiver relative to the shank after which the longitudinal connecting member can be inserted and the position of the receiver eventually locked with respect to movement relative to the shank.

The present invention is directed to such swivel head type bone screws and, in particular, to swivel head bone screws having an open head or receiver that allows placement of the longitudinal connecting member within the receiver and then subsequent closure by use of a closure top, plug or the like to capture the connector in the receiver of the screw.

SUMMARY OF THE INVENTION

A polyaxial bone anchor according to the invention includes a shank, a receiver, a lower compression or pressure insert and a retainer that operably cooperate with one another, the shank and the retainer being coupled and not pivotal or swivelable with respect to each other, but both equally swivelable with respect to the receiver until locked into place. The shank includes at least one lateral projection or spline that engages the retainer which is positioned below a top surface of the shank. In some embodiments, locking of the position of the shank with respect to the receiver is obtained by direct engagement between a bottom surface of a closure top and an upper surface of the lower pressure insert. The bone anchor is designed to allow the shank to be locked or secured in a selected angular configuration with respect to the receiver via the lower pressure insert, while locking or slidably capturing an elastic or inelastic longitudinal connecting member. The longitudinal connecting member may include, but is not limited to a hard rod or a softer deformable rod, a hard or deformable bar and even a cord. The longitudinal connecting member can be made of metallic or non-metallic material. The lower pressure insert exclusively contacts the shank at an upper surface thereof. The pressure insert remains spaced from the retainer in any and all selected angular configurations of the shank with respect to the receiver. With the polyaxial mechanism locked, the longitudinal connecting member, for example a rod or a cord, can either be locked in place or not locked and free to slide through the receiver. Freedom to slide through the locked receiver occurs if the rod or cord has a reduced diameter with respect to the pressure insert.

Objects of the invention include providing spinal implants and assemblies that have a low profile are easy to use and extremely effective for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an enlarged and exploded perspective view of a polyaxial bone screw assembly according to the invention including a bone screw shank, a receiver, a retaining structure, a lower pressure insert and a closure structure.

FIG. 2 is an enlarged top plan view of the shank of FIG. 1.

FIG. 3 is an enlarged front elevational view of the retainer of FIG. 1.

FIG. 4 is an enlarged top plan view of the retainer of FIG. 1.

FIG. 5 is an enlarged perspective view of the retainer of FIG. 1.

FIG. 6 is an enlarged top plan view of the lower pressure insert of FIG. 1.

FIG. 7 is an enlarged bottom plan view of the lower pressure insert of FIG. 1.

FIG. 8 is an enlarged cross-sectional view taken along the line 8-8 of FIG. 6.

DETAILED DESCRIPTION OF THE INVENTION

Figure 9B:
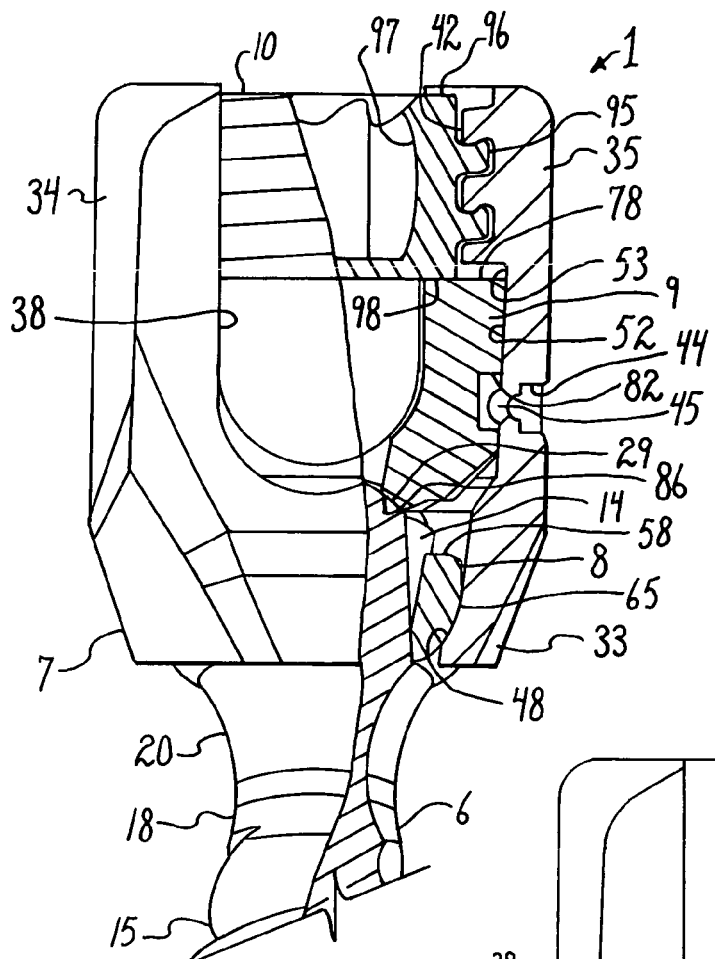
FIG. 9B is an enlarged and partial front elevational view of the bone screw assembly of FIG. 1 shown in an assembled, locked position (but without a longitudinal connecting member), with portions broken away to show the detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-12, the reference number 1 generally represents a polyaxial bone screw apparatus or assembly in accordance with the present invention operably utilized by implantation into a vertebra (not shown) and in conjunction with a longitudinal connecting member, such as an illustrated rod 3 so as to operably secure the rod 3 in a fixed position relative with respect to the vertebra (not shown).

The fully assembled bone anchor assembly 1 includes a shank 6, a receiver 7, a retainer structure or ring 8, a lower pressure insert 9 and a closure structure or top 10. With particular reference to FIGS. 1, 2 and 9-12, the shank 6 is elongate and has an upper body portion 14 integral with a lower body portion 15, ending in a tip 16. The shank body 15 has a helically wound bone implantable thread 17 extending from near the tip 16 to near the top 18 of the lower body 15 and extending radially outward therefrom. During use, the body 15 utilizing the thread 17 is implanted into a vertebra. The shank 6 has an elongated axis of rotation generally identified by the reference letter A.

Axially extending outward and upward from the shank body 15 is a neck 20, typically of reduced radius as compared to the adjacent top 18 of the body 15. Further extending axially and outwardly from the neck 20 is the shank upper portion 14 operably providing a connective or capture structure free from the bone or vertebra for joining with the receiver 7. With particular reference to FIG. 2, the shank upper portion or capture structure 14 has a radially outer cylindrical surface 22. The cylindrical surface 22 has at least one non-helically wound and radially outward or lateral extending projection or spline 24 that extends beyond the surface 22. In the embodiment shown in FIGS. 1-12, the shank upper portion 14 has three such laterally extending splines 24. It is noted that bone anchors of the invention have at least one and up to a plurality of splines 24. Preferably, the bone anchor includes from one to four splines. The splines 24 are located near and extend outwardly from an upper edge 25 of the shank upper portion cylindrical surface 22 and are equally circumferentially centered and spaced thereabout so as to be centered at approximately 120 degree intervals relative to each other. Each of the splines 24 has a substantially triangular shaped profile and a front wedge forming face 27 that slopes downwardly and radially inwardly from near the upper edge 25. Adjacent the upper edge 25 is a centrally located, axially extending and upwardly directed convex annular projection or dome-shaped upper end 29 that is centrally radiused. Each of the splines 24 includes an upper surface 30 that is adjacent to and extends from the upper end surface 29, having the same radius as the upper end surface 29. Also formed in the shank upper portion 14 within an annular rim 28 of the end surface 29 is a tool engagement aperture 31 for engagement by a tool driving head (not shown) that is sized and shaped to fit into the aperture 31 for both driving and rotating the shank 6 into a vertebra. In the illustrated embodiment, the aperture 31 is star-shaped and runs parallel to the axis A. It is foreseen that various sizes, shapes and numbers of apertures, slots or the like may be utilized in accordance with the invention for engaging a driving tool of suitable and similar mating shape. The illustrated shank 6 is cannulated, having a through bore 32 extending an entire length of the shank 6 along the axis A. The bore 32 is defined by an inner cylindrical wall of the shank 6 and has a circular opening at the shank tip 6 and an upper opening communicating with the internal drive feature 31. The bore 32 provides a passage through the shank 6 interior for a length of wire (not shown) inserted into the vertebra (not shown) prior to the insertion of the shank body 15, the wire providing a guide for insertion of the shank body 15 into the vertebra (not shown).

To provide a biologically active interface with the bone, the threaded shank body 15 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetracalcium phosphate ($Ca_4P_2O_9$), amorphous calcium phosphate and hydroxyapatite ($Ca_n(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With reference to FIG. 1, the receiver 7 has a generally squared-off U-shaped appearance with a partially cylindrical inner profile and a substantially faceted outer profile; however, the outer profile could also be of another configuration, for example, curved or cylindrical. A receiver axis of rotation B is aligned with the axis of rotation A of the shank 6 during assembly of the receiver 7 with the shank 6 and the retainer 8. After the receiver 7 is pivotally connected to the shank 6, and such assembly is implanted in a vertebra (not shown), the axis B is typically disposed at an angle with respect to the axis A of the shank 6.

With particular reference to FIGS. 1 and 9-12, the receiver 7 has a base 33 with a pair of upstanding arms 34 and 35 forming a U-shaped channel 38 between the arms 34 and 35 with a lower seat 39 having a slightly larger radius than the rod 3 for operably receiving the rod 3. The insert 9 that is disposed within the receiver 7 snugly receives the rod 3 as will be described more fully below. Each of the arms 34 and 35 has an interior surface 41 that includes a partial helically wound guide and advancement structure 42. In the illustrated embodiment, the guide and advancement structure 42 is a partial helically wound flangeform that mates under rotation with a similar structure on the closure top 10, as described below. However, it is foreseen that the guide and advancement structure 42 could alternatively be a buttress thread, a reverse angle thread or other thread like or non-thread like helically wound advancement structures for operably guiding under rotation and advancing the closure top between the arms 34 and 35. Tool engaging apertures 44 are formed on the outsides of the arms 34 and 35 for holding the receiver 7 during certain assembly steps and/or implantation of the assembly and also for access to a thin deformable wall 45 during assembly with the pressure insert 9.

A chamber or cavity 47 is located within the receiver base 33 that opens upwardly into the U-shaped channel 38. The cavity 47 includes a partial spherical shaped surface 48, at least a portion of which forms a partial internal hemispherical seat for the retainer 8, as is described further below. The hemispherical shaped surface 48 has a second radius associated therewith. A lower neck 50 defining a lower bore further communicates between the cavity 47 and the bottom exterior of the base 33 and is coaxial with the rotational axis B of the receiver 7. The neck 50 at least partially defines a restriction having a radius which is smaller than the radius of the retainer 8, so as to form a restrictive constriction at the location of the neck 50 relative to the retainer 8 to prevent the retainer 8 from passing between the cavity 47 and the lower exterior of the receiver 7. In an upper portion of the cavity 47, adjacent to the spherical surface 48, is a substantially cylindrical surface 52 that includes a run-out surface 53 located directly beneath the guide and advancement structure 42.

With particular reference to FIGS. 3-5, the retainer 8 is substantially ring-shaped and has an operational central axis which is the same as the elongate axis A associated with the shank 6, but when the retainer 8 is separated from the shank 6, the axis of rotation is identified as axis C. The retainer 8 has a central bore 57 that passes entirely through the retainer 8 from a top surface 58 to a bottom surface 59 thereof. The bore 57 is sized and shaped to fit snugly but slidably over the shank capture structure cylindrical surface 22 in such a manner as to allow sliding axial movement therebetween under certain conditions, as described below. Three axially aligned channels 60 are spaced from the axis C and extend radially outward from the bore 57 and into the wall of the retainer 8 so as to form three top to bottom grooves or slots therein. Backs 61 of the channels 60 are the same radial distance from the axis C as the distance the outermost portion of the splines 24 extend from the axis A of the shank 6. The channels 60 are also circumferentially angularly spaced equivalent to and have a width that corresponds with the splines 24. In this manner, the shank upper portion 14 can be uploaded into the retainer 8 by axially sliding the shank upper portion 14 through the retainer 8 central bore 57 whenever the splines 24 are aligned with the channels 60 or are in an aligned configuration. The details of assembly and subsequent cooperation between the shank 6, the retainer 8 and the receiver 7 are described in detail in Applicant's U.S. Pat. No. 6,716,214 issued Apr. 6, 2004, the entire disclosure of which is incorporated by reference herein.

The retainer 8 also has three capture partial slots, holding pockets, receivers or recesses 62 which extend radially outward from the upper part of the bore 57 and that do not extend the entire length from top to bottom of the retainer 8, but rather only open on the top surface 58 and extend partly along the height of the retainer 8 thereof. The holding pockets or recesses 62 are sized and positioned and shaped to receive the splines 24 from above when the splines 24 are in a non-aligned configuration relative to the channels 60. That is, each of the recesses or pockets 62 has a width that approximates the width of the splines 24 and has a mating wedge engaging surface 64 that is shaped similar to the spline wedge forming faces 27, so that the splines 24 can be slidably received into the recesses 62 from above by axially translating or moving the shank 6 downward relative to the retainer ring 8 when the splines 24 are positioned above the recesses 62 in a recess aligned configuration. In some embodiments, the wedge engaging faces 64 slope slightly greater than the wedge forming faces 27 on the splines 24 so that there is additional outward wedging that takes place when the splines 24 are urged downwardly into the recesses 62.

In this manner the shank upper portion 14 can be uploaded or pushed upwardly through the retainer central bore 57 so as to clear the top 58 of the retainer ring 8, rotated approximately 60 degrees and then downloaded or brought downwardly so that the splines 24 become located and captured in the recesses 62. Once the splines 24 are seated in the recesses 62 the shank 6 cannot move further axially downward relative to the retainer ring 8. Preferably, the retainer 8 is constructed of a metal or other material having sufficient resilience and elasticity as to allow the retainer 8 to radially expand slightly outward by downward pressure of the splines 24 on the recesses 62 under pressure from structure above, as will be discussed further below. This produces a slight outward radial expansion in the retainer ring 8 at the location of the recesses 62.

The retainer 8 has a radially outer partial hemispherical shaped surface 65 sized and shaped to mate with the partial spherical shaped surface 48 and having a third radius approximately equal to the second radius associated with the surface 48. The retainer 8 third radius is substantially larger than the radius associated with the annular curved surface 29 of the shank upper portion 14 and also substantially larger than the radius of the receiver neck 50.

Figure 12:
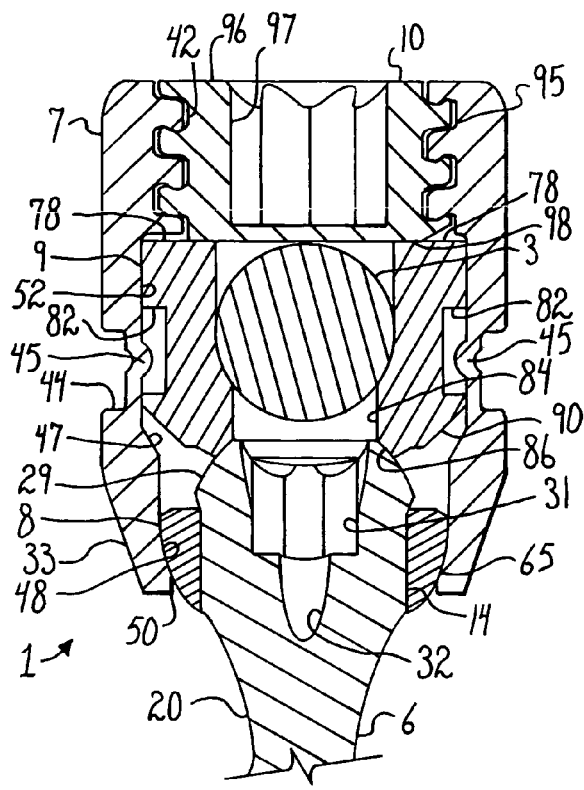
FIG. 12 is an enlarged and partial cross-sectional view taken along the line 12-12 of FIG. 11.

With particular reference to FIGS. 6-8, the lower compression or pressure insert 9 includes a substantially cylindrical body 70 integral with a pair of upstanding arms 72. The body 70 and arms 72 form a generally U-shaped, open, through-channel 74 having a lower seat 76 sized and shaped to closely, snugly engage the rod 3. As shown in the alternative embodiment of FIGS. 13-15, the insert 9 may be configured to include planar holding surfaces that closely hold a square or rectangular bar as well as hold a cylindrical rod-shaped or corded longitudinal connecting member. The arms 72 disposed on either side of the channel 74 extend outwardly from the body 70. The arms 72 are sized and configured for placement near the run-out 53 below the guide and advancement structure 42 at the receiver inner arms 34 and 35. As will be discussed in greater detail below, each of the arms 72 includes a top surface 78 ultimately located directly beneath the guide and advancement structure 42 and are directly engaged by the closure top 10 for locking the polyaxial mechanism of the assembly 1, even without a longitudinal connecting member as shown in FIG. 9B. Therefore, the assembly 1 may be used with a wide variety of longitudinal connecting members, including rods that engage the closure top 10 and are locked into position by such closure top 10 as well as rods of smaller diameter or cords that are captured by the closure top 10, but are otherwise movable within the receiver 7 and are thus in slidable or spaced relation with the closure top 10. In this manner, the locked polyaxial open screw can function like a closed, fixed monoaxial screw. Each arm 72 further includes a partially cylindrical outer surface 80 sized and shaped to fit within the receiver 7 at the guide and advancement structure 42 run-out relief 53. The cylindrical surfaces 80 are disposed substantially perpendicular to the respective adjacent top surfaces 78. In some embodiments of the invention recesses are formed near and/or at the top surfaces 78 and the surfaces that form the channel 74 to provide relief for material flow of the longitudinal connecting member, when, for example, the connector is made from a deformable plastic or elastic or inelastic polymer. For example, a recessed surface or groove may be directed downwardly and inwardly toward the channel 74. Each of the outer surfaces 80 further includes a recess 82 sized and shaped to receive holding tabs or crimped material from the receiver 7. As illustrated in FIG. 12, for example, the thin walls 45 of the receiver 7 are pressed into the recesses 82 to prevent rotation of the insert 9 about the axis B with respect to the receiver 7. In other embodiments of the invention, the receiver 7 may be equipped with spring tabs that snap into the recesses 82 to hold the insert 9 in place with respect to rotation. The recesses 82 are oval or elongate such that some desirable upward and downward movement of the insert 9 along the axis B of the receiver 7 is not prohibited.

The compression insert 9 further includes an inner cylindrical surface 84 that forms a through bore sized and shaped to receive a driving tool (not shown) therethrough that engages the shank drive feature 31 when the shank body 15 is driven into bone. The inner surface 84 runs between the seating surface 76 and an inner curved, annular, radiused or semi-spherical surface 86. The surface 86 is sized and shaped to slidingly and pivotally mate with and ultimately fix against the annular domed surface 29 of the shank upper portion 14. Thus, a radius of the surface 86 is the same or substantially similar to the radius of the surface 29. The surface 86 may include a roughening or surface finish to aid in frictional contact between the surface 86 and the surface 29, once a desired angle of articulation of the shank 6 with respect to the receiver 7 is reached. Adjacent to the inner surface 86 is a bottom rim or edge 88. Adjacent to the outer cylindrical surface 80 of the arms 72 is a substantially conical surface 90 that extends inwardly toward the lower rim 88. The surface 90 includes portions of the arms 72 as well as partially defining the pressure insert body 70. In some embodiments of the invention, the surface 90 terminates at the rim 88. In the illustrated embodiment, the insert 9 is further trimmed near the base rim 88 to ensure clearance between the insert 9 and the retainer 8. Specifically a v-shaped cut is formed in the insert 9 near the rim 88, the cut being defined by sloping surfaces 92 and 93. The surface 92 is adjacent the base rim 88 and the surface 93 is located between the surface 92 and the surface 90.

The pressure insert body 70 located between the arms 72 has an outer diameter slightly smaller than a diameter between crests of the guide and advancement structure 42 of the receiver 7 allowing for top loading of the compression insert 9 into the receiver 7 through the U-shaped channel 38, with the arms 72 being located between the arms 34 and 35 during insertion of the insert 9 into the receiver 7. Once located between the guide and advancement structure 42 and the shank upper portion 14, the insert 9 is rotated into place about the axis B until the arms 72 are directly below the guide and advancement structure 42 at or near the run-out 53. After the insert 9 is rotated into such position, a tool (not shown) may be inserted into the receiver apertures 44 to press the thin receiver walls 45 into the insert recesses 82. The lower compression insert 9 is sized such that the insert 9 is ultimately received within the cylindrical surface 52 of the receiver 7 below the guide and advancement structure 42. The receiver 7 fully receives the lower compression insert 9 and blocks the structure 9 from spreading or splaying in any direction. It is noted that assembly of the shank 6 with the retainer 8 within the receiver 7, followed by insertion of the lower compression insert 9 into the receiver 7 are assembly steps typically performed at the factory, advantageously providing a surgeon with a polyaxial bone screw with the lower insert 9 already held in alignment with the receiver 7 and thus ready for insertion into a vertebra.

The compression or pressure insert 9 ultimately seats on the shank upper portion 14 and is disposed substantially in the upper cylindrical portion 52 of the cavity 47, with the receiver deformable walls 45 engaging the insert 9 at the recesses 82, thereby holding the insert 7 in desired alignment with respect to the longitudinal connecting member 3. The assembly may be configured so that the insert 9 extends at least partially into the U-shaped channel 38 such that the seating surface 76 substantially contacts and engages an adjacent surface of the rod 3 when the rod 3 is placed in the receiver 7 and the closure structure or top 10 is tightened against the rod, the illustrated rod 3 being fixedly held in spaced relation with the lower seat 39 of the receiver 7. As will be further noted below, in some embodiments, a cord or smaller diameter rod may be held in sliding engagement with the insert 9, the shank 6 being locked into a desired position by engagement of the closure top 10 with the insert 9 and engagement of the insert 9 with the shank upper portion 14, which in turn presses the retainer 8 against the receiver seating surface 48.

Figure 11:
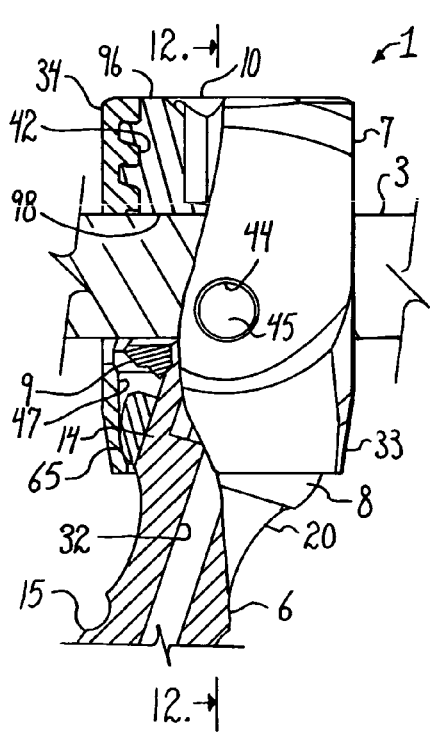
FIG. 11 is an enlarged and partial side elevational view of one of the bone screws of FIG. 10 and the rod, with portions broken away to show the detail thereof.
Figure 10:
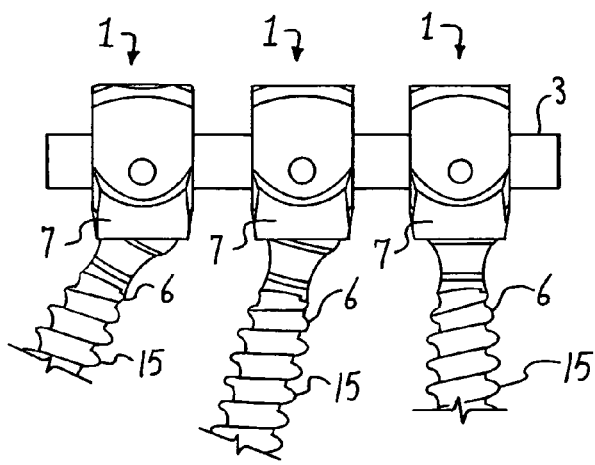
FIG. 10 is an enlarged and partial side elevational view, showing three bone screws of FIG. 1 and a longitudinal connecting member in the form of a rod.

With particular reference to FIGS. 10-12, the elongate connecting member illustrated in the drawing figures is a hard, inelastic solid cylindrical rod 3 of circular cross-section the diameter of which can vary depending on the application. However, longitudinal connecting members for use with the assembly 1 may take a variety of shapes, including but not limited to rods or bars of oval, rectangular or other curved or polygonal cross-section. In the alternative, the size and shape of the insert 9 channel may be modified so as to loosely hold or more closely hold, and if desired, fix the longitudinal connecting member to the assembly 1. The assembly 1 may also be used with an elastic tensioned cord. Such a cord may be made from a variety of materials, including polyester or other plastic fibers, strands or threads, such as polyethyleneterephthalate. In any event, the polyaxial screw can be securely locked when using any of the longitudinal connecting members. Furthermore, the longitudinal connector 3 may be a component of a longer overall dynamic stabilization connecting member, with cylindrical or bar-shaped portions sized and shaped for being received by the compression insert 9 of the receiver 7 having a u-shaped channel (or rectangular- or other-shaped channel) for loosely or more closely receiving the longitudinal connecting member. The longitudinal connecting member 3 may be integral or otherwise fixed to a bendable or damping component that is sized and shaped to be located between adjacent pairs of bone screw assemblies 1, for example. A damping component or bumper may surround and/or be attached to the member 3 at one or both sides of the bone screw assembly 1 and the bumper may engage the screw head. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonateurethane elastomers.

With reference to FIGS. 1 and 10-12, the closure structure or closure top 10 can be any of a variety of different types of closure structures for use in conjunction with the present invention with suitable mating structure on the upstanding arms 34 and 35. In the embodiment shown, the closure top 10 is rotatably received between the spaced arms 34 and 35 of the receiver 7. The illustrated closure structure 10 is substantially cylindrical and includes an outer helically wound guide and advancement structure 95 in the form of a flange form that operably joins with the guide and advancement structure 42 of the receiver 7. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 10 downward between the arms 34 and 35 and having such a nature as to resist splaying of the arms 34 and 35 when the closure structure 10 is advanced into the channel 38. The illustrated closure structure 10 also includes a top surface 96 with an internal drive 97 in the form of an aperture that is illustrated as a star-shaped internal drive, but may be, for example, a hex-shaped drive or other internal drives, including, but not limited to slotted, tri-wing, spanner, two or more apertures of various shapes, and the like. A driving tool (not shown) sized and shaped for engagement with the internal drive 97 is used for both rotatable engagement and, if needed, disengagement of the closure 10 from the receiver arms 34 and 35. It is also foreseen that the closure structure 10 may alternatively include a break-off head designed to allow such a head to break from a base of the closure at a preselected torque, for example, 70 to 140 inch pounds. Such a closure structure would also include a base having an internal drive to be used for closure removal. A bottom surface 98 of the closure top 10 is planar, but could be domed or radiused and may include a point, points, a rim or roughening for engagement with the rod 3. Furthermore, in some embodiments, the closure top may include an extended base, central cylinder, cap or knob for pressing into a deformable rod or compressing a cord or cable against the insert seating surface. Such an extension or knob would be sized and shaped to extend into the channel 74 of the insert and also clear the walls defining the channel 74 so that a portion of the closure top still abuts against the insert 9, locking the polyaxial mechanism of the bone screw.

The illustrated bottom surface 98 of the closure top 10 is sized and shaped for engagement with the top planar surfaces 78 of the arms 72 of the lower pressure or compression insert 9. As illustrated in FIG. 9B, engagement of the surface 98 with the surfaces 78 independently locks the polyaxial mechanism of the bone screw 1, the insert 9 being pushed downwardly toward the shank upper portion 14 by the closure 10 that in turn presses the retainer 8 against the receiver 7 at the seating surface 48. In some embodiments of the invention, and as illustrated in FIGS. 11 and 12, the surface 98 of the closure top 10 also can barely touch or firmly frictionally engage the rod 3, capturing and/or locking the rod in position between the closure top 10 and the insert 9. In other embodiments of the invention, a smaller rod, cable or cord may remain in sliding engagement with the closure top 10 with the top 10 being only in frictional engagement with the insert 9 to lock the polyaxial mechanism of the assembly 1 and fix the angular configuration of the shank 6 with respect to the receiver 7 without fixing the rod, cable or cord captured by the receiver 7 and between the insert and the closure top 10. Also, depending upon the material of the rod 3, with time, the rod 3 may undergo creep or other plastic deformation that may lessen the engagement between the cylindrical surface of the rod 3 and the closure surface 98. However, regardless of any movement and/or change in position or angulation of the rod with respect to the receiver, the frictional engagement between the closure member 10 and the lower compression insert 9, both preferably made from a metal or metal alloy, such as cobalt chrome, stainless steel or titanium, will remain rigid and secure.

The closure top 10 may further include a cannulation through bore extending along a central axis thereof and through a surface of the drive 97 and the bottom surface 98. Such a through bore provides a passage through the closure 10 interior for a length of wire (not shown) inserted therein to provide a guide for insertion of the closure top into the receiver arms 34 and 35, after which the wire could be removed and the rod, cable or cord could then be threaded or inserted through the receiver.

When the polyaxial bone screw assembly 1 is placed in use in accordance with the invention the retainer 8 is normally first slid through the receiver U-shaped channel 38 and into and seated in the receiver cavity 47. Thereafter, the retainer 8 is rotated 90 degrees so as to be coaxial with the receiver 7 and so that the retainer outer surface 65 snugly but slidably mates with the receiver interior spherical shaped surface 48. The retainer 8 in the receiver 7 is then slid over the shank upper portion 14 so that the splines 24 slide upwardly through and above respective channels 60 so that the splines 24 are then located, at least partially, in the U-shaped channel 38 and chamber 47 above the retainer ring 8. The shank 6 is then rotated 60 degrees relative to the receiver about the axis A and the translational direction of the shank 6 is reversed so that it goes downwardly or axially with respect to the receiver 7, and the splines 24 enter the recesses 62. At this point there is no substantial outward or downward pressure on the retainer 8 and so the retainer 8 is easily rotatable along with the shank 6 within the chamber 47 and such rotation is of a ball and socket type wherein the angle of rotation is only restricted by engagement of the neck 20 with the neck 50 of the receiver 7.

Figure 9A:
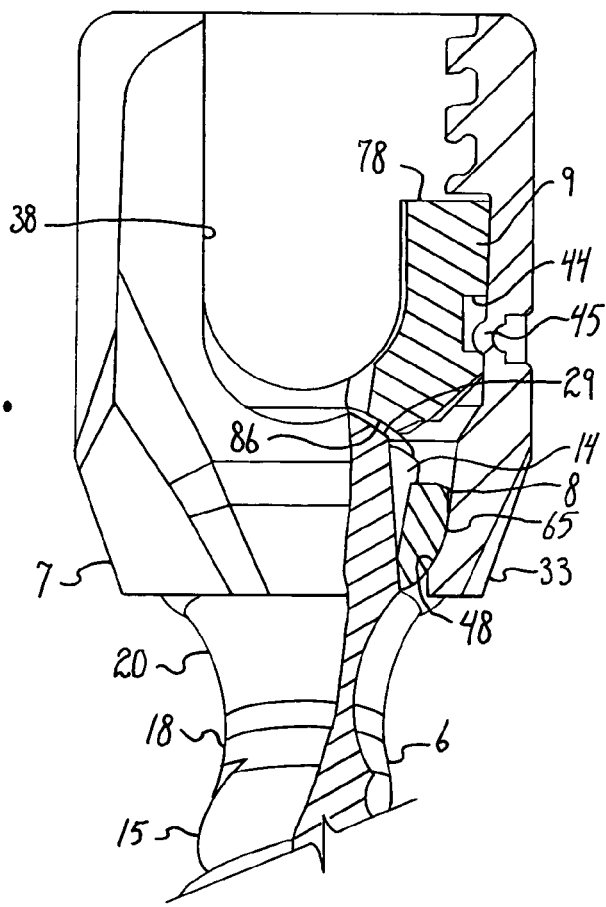
FIG. 9A is an enlarged and partial front elevational view of the bone screw assembly of FIG. 1 shown in a stage of assembly, with crimped projections of the receiver holding the insert in frictional engagement with the shank, the shank and retainer being in non-floppy frictional, but movable engagement with the receiver, with portions broken away to show the detail thereof.

Then, the insert 9 is inserted into the channel 38 with the arms 72 aligned in the channel 38 between the guide and advancement structures 42. The insert 9 is then moved downwardly in the channel 38 and toward the cavity 47. Once the arms 72 are located generally below the guide and advancement structure 42 and adjacent the run-out relief 53, the insert 9 is rotated about the axis B of the receiver 7. The arms 72 fit within the cylindrical walls 52 above the cavity 47. Once the arms 72 are located directly below the guide and advancement structures 42, rotation is ceased and a tool (not shown) is used to press the thin walls 45 of the receiver 7 into the recesses 82 of the insert 9. The insert 9 is now locked into place inside the receiver 7 with the guide and advancement structures 42 prohibiting upward movement of the insert 9 out of the channel 38 and the crimped walls 45 preventing rotation of the insert 9. As illustrated in FIGS. 9A, 9B, 11 and 12, the insert 9 seats on the shank upper portion 14 with the surface 86 in sliding engagement with the surface 29. The run-out or relief 53 is sized and shaped to allow for some upward and downward movement of the insert 9 toward and away from the shank upper portion 14 such that the shank 6 is pivotable with respect to the receiver 7 until the closure structure 10 presses on the insert 9 that in turn presses upon the upper portion 14 into locking frictional engagement with the receiver 7 at the surface 48. This assembly process is generally performed by the manufacturer. With particular reference to FIG. 9A, the walls 45 may be crimped at a location with respect to the insert aperture 44 that causes the surface 86 of the insert 9 to bias against and frictionally engage the shank domed surface 29 to provide a sub-assembly in which the shank 6 is pivotable with respect to the receiver 7, but in a non-floppy manner, making it easier for a surgeon to position the receiver 7 at a desired articulation with respect to the shank 6 and have the assembly hold such desired position prior to insertion of the rod 3 or other longitudinal connecting member.

The sub-assembly as shown in FIG. 9A is then normally screwed into a bone, such as vertebra, by rotation of the shank 6 using a suitable driving tool (not shown) that operably drives and rotates the shank 6 by engagement thereof at the internal drive 31. Normally, the receiver 7, retainer 8 and insert 9 are assembled on the shank 6 before placing the shank 6 in the vertebra, but in certain circumstances, the shank 6 can be first implanted with the capture structure 14 extending proud to allow assembly and then the shank 6 can be further driven into the vertebra.

A rod 3 is eventually positioned within the receiver U-shaped channel 38, as is seen in FIGS. 10-12, and the closure top 10 is then inserted into and advanced between the arms 34 and 35 so as to bias or push against the insert 9 (and here, the rod 3 also). A driving tool (not shown) is inserted into the drive 97 to rotate and drive the closure top 10 into the receiver 7. The shank dome 29 is engaged by the insert 9 and pushed downwardly when the closure top 10 pushes downwardly on the insert 9, as is seen in FIG. 12. The downward pressure on the shank 6 in turn urges the splines 24 downwardly which exerts both a downward and outward thrust on the retainer ring 8. Three polyaxial bone screws 1, including the rod 3, are shown in FIG. 10, illustrating various shank 6 to receiver 7 angular configurations. Furthermore, FIGS. 11 and 12 illustrate a particular angular configuration in which the axis A of the bone screw shank 6 is not coaxial with the axis B of the receiver 7 and the shank 6 is locked in this angular locked configuration.

If removal of the assembly 1 is necessary, the assembly 1 can be disassembled by using a driving tool mating with the closure top aperture 97 to rotate the closure top 10 and reverse the advancement thereof in the receiver 7. Then, disassembly of the remainder of the assembly 1 may be accomplished in reverse mode in comparison to the procedure described above for assembly.

Figure 13:
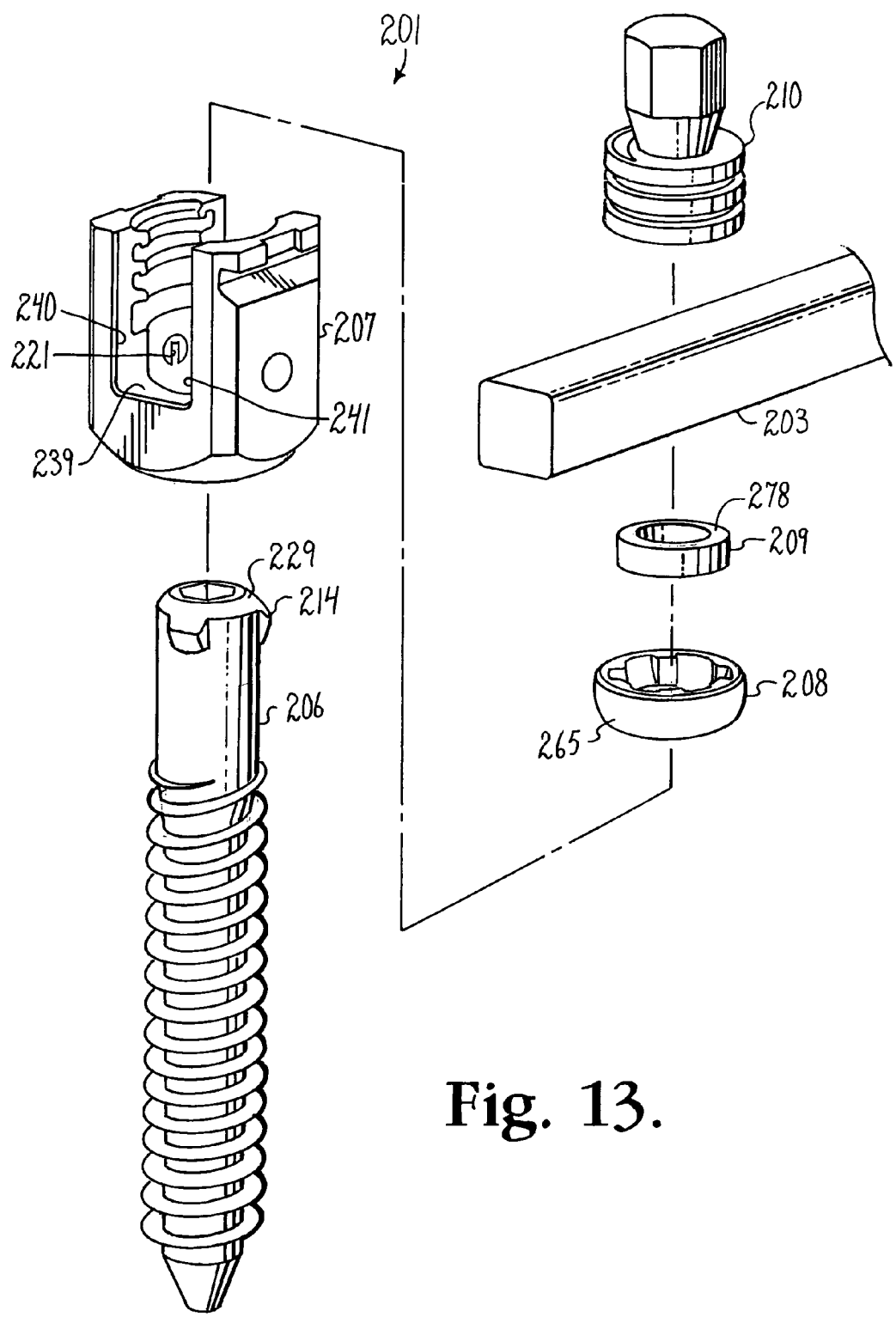
FIG. 13 is an enlarged and exploded perspective view of an alternative embodiment of a polyaxial bone screw assembly according to the invention including a bone screw shank, a receiver, a retaining structure, a cylindrical lower pressure insert and shown with a bar and a closure structure.
Figures 14, 15:
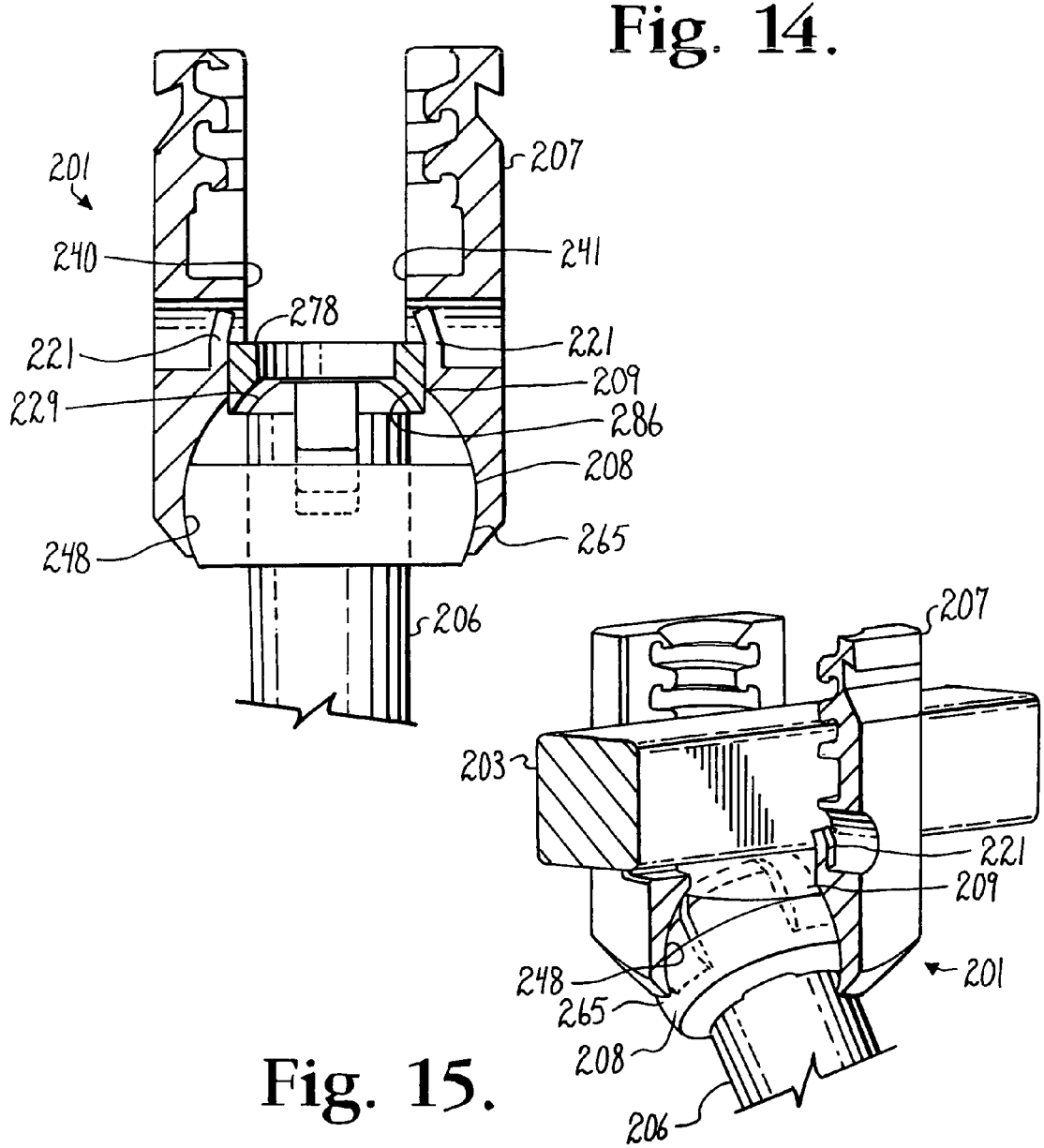
FIG. 14 is an enlarged and partial front elevational view of the shank, receiver, retaining structure and pressure insert of FIG. 13 with portions broken away to show the detail thereof.
FIG. 15 is an enlarged and partial perspective view of the shank, receiver, retaining structure, pressure insert and bar of FIG. 13 with portions broken away to show the detail thereof.

Illustrated in FIGS. 13-15 is a second embodiment of a bone screw assembly, generally 201, according to the present invention. The assembly includes a shank 206, a receiver 207, a retainer 208, a cylindrical lower pressure insert 209 and a closure top 210 having a break-off head. The assembly is shown with a longitudinal connecting member in the form of a bar 203. The shank 206 includes an upper portion 214 that is substantially similar in form and function to the portion 14 of the shank 6 of the assembly 1 and the retainer ring 208 is substantially similar in form and function to the retainer ring 8 of the assembly 1. The receiver 207 is somewhat similar to the receiver 7 of the assembly 1 and differences between the receiver 7 and the receiver 207 include the feature of spring tabs 221 for holding the insert 209 within the receiver 207 and planar seating surfaces 239, 240 and 241 for receiving the bar 203.

The pressure insert 209 includes a substantially cylindrical body with an outer cylindrical surface 280. The insert also includes a lower spherical surface 286 sized and shaped for slidably mating with an upper domed surface 229 of the shank upper portion 214. The insert 209 includes a planar top surface 278 upon which the bar 203 is received. In use, the closure top 210 presses upon the bar 203 that in turn presses upon the insert 209 that presses' directly upon the shank upper portion 229 and not upon the retainer 208. Downward movement of the shank upper portion 229 that is fixed to the retainer 208 then in turn presses an outer spherical surface 265 of the retainer 208 against an inner seating surface 248 of the receiver 207. As shown in FIG. 15, when the shank 206 is disposed at an angle with respect to the receiver 207, the insert 209 remains spaced from the retainer 208 and does not make contact with the retainer 208 in any angular configuration of the shank 206 with respect to the receiver 207.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone anchor comprising:
   a) a shank having a body for fixation to a bone and an integral upper portion, the upper portion having an upper end surface and at least one laterally directed projection;
   b) a receiver having a top portion and a base, the receiver top portion defining an open channel, the base having a seating surface partially defining a cavity, the channel communicating with the cavity, the cavity communicating with an external of the base through an opening sized and shaped to receive the shank upper portion therethrough;
   c) a compression insert disposed in the receiver, the insert having a lower mating surface that exclusively engages and applies downward pressure to the upper end surface of the shank upper portion; and
   d) a retainer having an external surface and a central bore with an internal surface defining the central bore having at least one substantially vertical channel for slideably receiving the projection therethrough and at least one pocket for downwardly receiving and holding the projection of the shank upper portion, the shank upper portion and the retainer being in fixed relation to one another, both the upper portion and the retainer being in swivelable relation within the receiver, providing selective angular positioning of the shank with respect to the receiver, the retainer external surface being in slidable engagement with the receiver seating surface during positioning, the retainer being spaced from the compression insert at any and all angular positions of the shank with respect to the receiver.

2. The bone anchor of claim 1 further comprising a closure top engaging the compression insert to lock the angular position of the shank with respect to the receiver.

3. The bone anchor of claim 1 wherein the receiver has a projected wall surface engaging the compression insert.

4. The bone anchor of claim 3 wherein the projected wall surface prevents rotational movement of the compression insert.

5. The bone anchor of claim 3 wherein the projected wall surface biases the compression insert into non-locking frictional engagement with the shank upper portion.

6. The bone anchor of claim 1 wherein the shank is cannulated.

7. The bone anchor of claim 1 wherein the shank has an internal drive feature.

8. A polyaxial bone screw assembly comprising:
a) a receiver having a channel adapted to receive an elongate longitudinal member and having a lower restrictive neck;
b) a compression insert located in the receiver and adapted to engage the elongate longitudinal member;
c) a shank having a lower portion adapted to be implanted in a bone of a patient and an upper portion having at least one laterally directed projection; the shank upper portion being sized and shaped to be positioned in the receiver so as to have the shank extend through the lower restrictive neck;
d) a retainer ring separate from the shank, received in the receiver and adjacent the lower restrictive neck; the retainer ring mating with and non-pivotably coupled to the shank upper portion by downward positioning of the laterally directed projection into a holding pocket in the retainer ring, the upper portion and retainer ring being polyaxially rotatable together through various angular configurations relative to the receiver prior to locking of the position of the shank relative to the receiver, the retainer ring width being larger than a width of the receiver lower restrictive neck so as to hold the shank upper portion in the receiver while allowing polyaxial movement of the shank relative to the receiver during positioning; and
e) the shank upper portion being sized, shaped and positioned to engage the compression insert and receive a downward force from the compression insert; the retainer being sized and shaped so as to be free from engagement with the compression insert in all angular configurations of the shank and retainer relative to the receiver.

9. The bone screw assembly of claim 8 wherein the retainer ring is spaced from and located below a top surface of the shank upper portion, the retainer ring being unengaged with the compression insert at any and all angular positions of the shank with respect to the receiver.

10. The bone screw assembly of claim 8 further comprising crimping structure on the receiver, the crimping structure engaging the compression insert and biasing the compression insert against the shank upper portion to provide positioning of the shank with respect to the receiver.

11. The bone screw assembly of claim 8 further comprising a closure top having mating structure for mating with the receiver and capturing a longitudinal connecting member in the receiver and wherein the compression insert is sized, shaped and positioned to receive a downward force from the closure top so as to lock the position of the shank relative to the receiver channel thereby locking of the position of the shank and the receiver relative to one another.

12. A polyaxial bone screw assembly comprising:
a) a receiver having a channel adapted to receive an elongate longitudinal member and having a lower opening;
b) a shank having a lower portion adapted to be implanted in a bone of a patient and an upper portion, the shank upper portion having at least one laterally directed projection and being sized and shaped to be positioned in the receiver so as to extend through the lower opening;
c) a retaining structure non-integral with the shank and loaded into the receiver separately from the shank, the retaining structure mating with and being secured to the shank by downward positioning of the laterally directed projection into a holding pocket in the retaining structure so as to capture and pivot the retaining structure with the shank upper portion in the receiver so as to allow polyaxial movement of the shank relative to the receiver; and
d) a compression insert directly and frictionally engaging the shank upper portion and being in spaced relation with respect to the retaining structure in all positions of the retainer structure with respect to the receiver.

13. The assembly of claim 12 further comprising a closure top engaging the compression insert to lock the angular position of the shank with respect to the receiver.

14. A polyaxial bone screw assembly comprising:
a) an elongate longitudinal connecting member;
b) a receiver having a channel for receiving the connecting member during use and having a lower bore and a lower opening;
c) a shank having a lower portion adapted to be implanted in a bone of a patient and an upper portion, the upper portion having at least one laterally directed projection and being sized and shaped to be loaded into the receiver through the lower opening;
d) a compression insert located in the receiver, the insert in engagement with the connecting member and with the shank upper portion;
e) a retainer ring separate from the shank and received in the receiver, the retainer ring mating with and secured to the shank upper portion by downward positioning of the laterally directed projection into a holding pocket in the retainer ring so as to rotate the ring together with the shank relative to the receiver during positioning, the compression insert, retainer ring and shank upper portion forming a subassembly prior to locking of the position of the shank relative to the receiver, the subassembly presenting a receiver engaging surface so as to hold the shank in the receiver while allowing polyaxial movement of the shank relative to the receiver during positioning; the retainer ring being free from engagement with the compression insert throughout all polyaxial movement of the shank relative to the receiver;
f) a closure including mating structure for mating with the receiver and closing the channel so as to capture the longitudinal connecting member in the channel; and g) the shank upper portion being sized, shaped and positioned such that upon assembly of the bone screw and the longitudinal connecting member, the shank upper portion receives a force generated by the closure that causes frictional engagement of the retainer ring with the receiver so as to secure the shank in a selected fixed angular configuration relative to the receiver.

15. A polyaxial bone anchor comprising:
a) a shank having a body for fixation to a bone and an integral upper portion, the upper portion having an upper end surface and at least one laterally directed projection;
b) a receiver having a top portion and a base, the receiver top portion defining an open channel, the base having a seating surface partially defining a cavity, the channel communicating with the cavity, the cavity communicating with an external of the base through an opening;
c) a compression insert disposed in the receiver, the insert having a mating surface exclusively frictionally engageable with the upper end surface of the shank upper portion; and
d) a retainer having an external surface and a central bore with an internal surface defining the central bore having at least one substantially vertical channel for slideably receiving the projection therethrough and at least one pocket for downwardly receiving and holding the projection of the shank upper portion, the shank upper portion and the retainer being in fixed relation to one another, both the upper portion and the retainer being in swivelable relation within the receiver, providing selective angular positioning of the shank with respect to the receiver, the retainer external surface being in slidable engagement with the receiver seating surface, the retainer being spaced from the compression insert at any and all angular positions of the shank with respect to the receiver.

16. A polyaxial bone anchor comprising:
a) a shank with an outward projection at an upper end thereof;
b) a receiver body having a lower opening through which the shank is received, an interior chamber and an upper channel adapted to receive a rod member;
c) a retainer that is received in the receiver chamber; the retainer being secured to the shank such that the shank and the retainer polyaxially rotate together during positioning of the shank relative to the receiver; and
d) a pressure insert that is received in the receiver chamber above the shank such that the pressure insert applies downward force from above against the shank, but does not engage the retainer during polyaxial rotation of the shank relative to the receiver.

* * * * *